(12) United States Patent
Tuiten

(10) Patent No.: US 9,700,566 B2
(45) Date of Patent: *Jul. 11, 2017

(54) PHARMACEUTICAL FORMULATIONS AND USES THEREOF IN THE TREATMENT OF FEMALE SEXUAL DYSFUNCTION

(71) Applicant: EB IP LYBRIDO B.V., Almere (NL)

(72) Inventor: Jan Johan Adriaan Tuiten, Almere (NL)

(73) Assignee: EB IP LYBRIDO B.V., Almere (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/866,547

(22) Filed: Sep. 25, 2015

(65) Prior Publication Data

US 2016/0015720 A1  Jan. 21, 2016

Related U.S. Application Data

(60) Division of application No. 13/529,813, filed on Jun. 21, 2012, now Pat. No. 9,192,669, which is a division of application No. 11/595,778, filed on Nov. 10, 2006, now Pat. No. 8,227,453, which is a continuation of application No. PCT/NL2005/000355, filed on May 11, 2005.

(30) Foreign Application Priority Data

| May 11, 2004 | (EP) | 04076402 |
| Nov. 4, 2004 | (EP) | 04078033 |
| Dec. 13, 2004 | (EP) | 04078380 |
| Dec. 13, 2004 | (EP) | 04078381 |
| Dec. 21, 2004 | (EP) | 04078455 |

(51) Int. Cl.

| A61K 31/568 | (2006.01) |
| A61K 31/53 | (2006.01) |
| A61K 31/724 | (2006.01) |
| A61K 45/06 | (2006.01) |
| A61K 9/00 | (2006.01) |
| A61K 31/4985 | (2006.01) |
| A61K 31/519 | (2006.01) |
| A61K 47/40 | (2006.01) |
| G06Q 50/22 | (2012.01) |

(52) U.S. Cl.
CPC .......... *A61K 31/568* (2013.01); *A61K 9/006* (2013.01); *A61K 31/4985* (2013.01); *A61K 31/519* (2013.01); *A61K 31/53* (2013.01); *A61K 31/724* (2013.01); *A61K 45/06* (2013.01); *A61K 47/40* (2013.01); *G06Q 50/22* (2013.01)

(58) Field of Classification Search
CPC .... A61K 31/568; A61K 31/53; A61K 31/724; A61K 31/4985; A61K 31/519; A61K 45/06; A61K 47/40; A61K 9/006; C07D 267/14; C07D 413/06; G06Q 50/22

See application file for complete search history.

(56) References Cited

U.S. PATENT DOCUMENTS

| 3,976,776 A | 8/1976 | Wu et al. |
| 4,521,421 A | 6/1985 | Foreman |
| 4,596,795 A | 6/1986 | Pitha |
| 4,640,921 A | 2/1987 | Othmer et al. |
| 4,833,142 A | 5/1989 | Hartog et al. |
| 4,877,774 A | 10/1989 | Pitha et al. |
| 5,015,646 A | 5/1991 | Simms |
| 5,250,534 A | 10/1993 | Bell et al. |
| 5,389,687 A | 2/1995 | Schaus et al. |
| 5,565,466 A | 10/1996 | Gioco et al. |
| 5,731,339 A | 3/1998 | Lowrey |
| 5,877,216 A | 3/1999 | Place et al. |
| 6,165,975 A | 12/2000 | Adams et al. |
| 6,242,436 B1 | 6/2001 | Llewellyn |
| 6,246,436 B1 | 6/2001 | Lin et al. |
| 6,251,436 B1 | 6/2001 | Drizen et al. |
| 6,294,550 B1 | 9/2001 | Place et al. |
| 6,306,841 B1 | 10/2001 | Place et al. |
| 6,423,683 B1 | 7/2002 | Heaton et al. |
| 6,428,769 B1 | 8/2002 | Rubsamen et al. |
| 6,469,012 B1 | 10/2002 | Ellis et al. |
| 6,469,016 B1 | 10/2002 | Place et al. |
| 6,472,434 B1 | 10/2002 | Place et al. |
| 6,541,536 B2 | 4/2003 | Weikard et al. |
| 6,593,313 B2 | 7/2003 | Place et al. |
| 6,608,065 B1 | 8/2003 | Daugan |
| 6,610,652 B2 | 8/2003 | Adams et al. |
| 6,632,419 B2 | 10/2003 | Rubsamen et al. |
| 6,964,780 B1 | 11/2005 | King et al. |
| 7,151,103 B2 | 12/2006 | Borsini et al. |
| 7,198,801 B2 | 4/2007 | Carrara et al. |
| 2002/0002973 A1 | 1/2002 | Rubsamen et al. |
| 2003/0022877 A1 | 1/2003 | Dudley |

(Continued)

FOREIGN PATENT DOCUMENTS

| AU | 200062635 | 6/2005 |
| EP | 2000143 | 12/2008 |

(Continued)

OTHER PUBLICATIONS

Chen, "Practical Technology of Pharmaceutical Adjuvants," Henan University Press (2001) version 1, 3 pages.
Decision of Reexamination for Chinese Application No. 2012100087326, issued Mar. 15, 2016, 6 pages.
Gong et al., "Pharmacy," Jiangsu Science and Technology Press (1998) version 1, 2 pages.
Zhang, "Pharmacology," People's Medical Publishing House (2004) version 5, 3 pages.
Zheng, "Clinic Biochemical Assay," China Medical Science Press (2004) version 1, 3 pages.
Amstislavskaya et al., "Effect of serotonin 5-HT1A receptor agonists on sexual motivation of male mice," Bull Exp Biol Med (1999) 127(2):203-205.

(Continued)

*Primary Examiner* — Sarah Pihonak
(74) *Attorney, Agent, or Firm* — Morrison & Foerster LLP

(57) ABSTRACT

The present invention relates to the use of a combination of a PDE5-inhibitor and testosterone for the preparation of a medicament for the treatment of Female Sexual Dysfunction.

9 Claims, 5 Drawing Sheets

(56) References Cited

U.S. PATENT DOCUMENTS

| | | |
|---|---|---|
| 2003/0027801 A1 | 2/2003 | McBurney |
| 2003/0027804 A1 | 2/2003 | Van der Hoop |
| 2003/0104980 A1 | 6/2003 | Borsini et al. |
| 2003/0139384 A1 | 7/2003 | Dudley |
| 2004/0014761 A1 | 1/2004 | Place et al. |
| 2004/0186086 A1 | 9/2004 | Bunschoten et al. |
| 2004/0208829 A1 | 10/2004 | Rubsamen et al. |
| 2005/0152956 A1 | 7/2005 | Dudley |
| 2005/0245539 A1 | 11/2005 | Mendla et al. |
| 2006/0040935 A1 | 2/2006 | Maytorn et al. |
| 2006/0270642 A1 | 11/2006 | Lehman et al. |
| 2006/0281752 A1 | 12/2006 | Heaton et al. |
| 2006/0287335 A1 | 12/2006 | Sukoff Rizzo et al. |
| 2007/0093450 A1 | 4/2007 | Tuiten |
| 2007/0149454 A1 | 6/2007 | Mattern |
| 2007/0154533 A1 | 7/2007 | Dudley |
| 2009/0306026 A1 | 12/2009 | Tuiten et al. |
| 2010/0093680 A1 | 4/2010 | Tuiten et al. |
| 2010/0152145 A1 | 6/2010 | Tuiten et al. |
| 2010/0160270 A1 | 6/2010 | Tuiten et al. |

FOREIGN PATENT DOCUMENTS

| | | |
|---|---|---|
| JP | 11-504902 | 5/1999 |
| JP | 2001-520999 | 11/2001 |
| JP | 2002-543128 | 12/2002 |
| JP | 2003-530430 | 10/2003 |
| JP | 2004-520320 | 7/2004 |
| JP | 2005-500347 | 1/2005 |
| JP | 2005-503374 | 2/2005 |
| NZ | 524601 | 4/2006 |
| RU | 2130776 | 5/1999 |
| RU | 97117167 | 10/1999 |
| RU | 2152787 | 7/2000 |
| RU | 2180591 | 3/2002 |
| RU | 2285519 | 10/2006 |
| WO | WO-94/28902 | 12/1994 |
| WO | WO-95/05188 | 2/1995 |
| WO | WO-95/33486 | 12/1995 |
| WO | WO-96/28142 | 9/1996 |
| WO | WO-96/33705 | 10/1996 |
| WO | WO-96/36339 | 11/1996 |
| WO | WO-97/03675 | 2/1997 |
| WO | WO-99/21562 | 5/1999 |
| WO | WO-99/62502 | 9/1999 |
| WO | WO-00/66084 | 11/2000 |
| WO | WO-00/66114 | 11/2000 |
| WO | WO-01/78703 | 10/2001 |
| WO | WO-02/26214 | 4/2002 |
| WO | WO-02/051420 | 7/2002 |
| WO | WO-02/069906 | 9/2002 |
| WO | WO-03/011300 | 2/2003 |
| WO | WO-03/011301 | 2/2003 |
| WO | WO-03/002123 | 9/2003 |
| WO | WO-2004/037173 | 5/2004 |
| WO | WO-2004/037262 | 5/2004 |
| WO | WO-2005/007166 | 1/2005 |
| WO | WO-2005/039530 | 5/2005 |
| WO | WO-2005/094827 | 10/2005 |
| WO | WO-2005/102342 | 11/2005 |
| WO | WO-2005/107810 | 11/2005 |
| WO | WO-2006/127057 | 11/2006 |
| WO | WO-2007/054791 | 5/2007 |
| WO | WO-2007/055563 | 5/2007 |

OTHER PUBLICATIONS

Angulo et al., "Vardenafil enhances clitoral and vaginal blood flow responses to pelvic nerve stimulation in female dogs," Int J Impot Res (2003) 15(2):137-141.

Ansel, "The Prescription," in Remington's Pharmaceutical Sciences, 17th Ed. (1985), Gennaro, (ed.), Chapter 101, pp. 1778-1787.

Belikov et al., Pharmaceutical Chemistry (1993) 43-47 (machine translation provided).

Berman et al., "Safety and Efficacy of Sildenafil Citrate for the Treatment of Female Sexual Arousal Disorder: A Double-Blind, Placebo Controlled Study," Journal of Urology (2003) 170(6):2333-2338.

Doggrell, "Comparison of Clinical Trials with Sildenafil, Vardenafil and Tadalafil in Erectile Dysfunction," Expert Opin. Pharmacother. (2005) 6(1):1-2. (abstract).

Dyson et al., May's Chemistry of Synthetic Drugs, (5th ed. 1959) (machine translation provided).

Fourcroy, "Female Sexual Dysfunction Potential for Pharmacotherapy," Drugs (2003) 63:1445-1457.

Frye et al., "Behavioral Effects of 3 Alpha-Androstanediol.1: Modulation of Sexual Receptivity and Promotion of GABA-Stimulated Chloride Flux," Behav. Brain Res. (1996) 79 (1-2):109-118. (abstract).

Graham-Smith et al., Oxford Handbook of Clinical Pharmacology and Pharmacotherapy (2000) 18-20 (machine translation provided).

Haensel et al., "Flesinoxan: A Prosexual Drug for Male Rats," European Journal of Pharmacology (1997) 330:1-9.

Holterhus et al., "Anabolic steroids, testosterone-precursors and virilizing androgens induce distinct activation profiles of androgen responsive promoter constructs," J Steroid Biochem Mol Biol (2002) 82:269-275.

International Preliminary Report on Patentability for PCT/NL2007/050533, mailed Jul. 2, 2009, 8 pages.

International Search Report for PCT/NL2007/050533, mailed on Feb. 25, 2009, 3 pages.

International Preliminary Report on Patentability for International Patent Application No. PCT/NO2007/050534, mailed Jul. 2, 2009, 8 pages.

International Search Report for International Patent Application No. PCT/NO2007/050534, mailed Feb. 24, 2009, 3 pages.

International Preliminary Report on Patentability for International Patent Application No. PCT/NO2007/050535, mailed Jul. 2, 2009, 9 pages.

International Search Report for International Patent Application No. PCT/NO2007/050535, mailed Feb. 24, 2009, 3 pages.

International Search Report for International Patent Application No. PCT/NL2005/000355, mailed Dec. 18, 2006, 5 pages.

International Search Report for International Patent Application No. PCT/NL2006/000542, mailed Jul. 17, 2007, 5 pages.

Kharkevich et al., Pharmacology (3rd ed. 1987) 41-42 (machine translation provided).

Koolman et al., Biochemistry (1998) 365 (machine translation provided).

Kuhn, "Anabolic Steroids," Rec. Progress Hormone Research (2002) Academic Press vol. 57, pp. 411-434.

Kurashina et al., "Pharmaceutical Society of Japan," Pharmacia (1999) 35(8):820.

Morali et al., (1994) "Mechanisms Regulating Male Sexual Behavior in the Rat: Role of 3α- and 3β-Androstanediols," Biology of Reproduction 51:562-571.

Ottani et al., "Modulatory activity of sildenafil on copulatory behavior of both intact and castrated male rats," Pharmacology, Biochemistry and Behavior (2002) 72:717-722.

Phillips, "Female Sexual Dysfunction: Evaluation and Treatment," Am Fam Physician (2000) 62(1): 127-136, 141-142.

Rasia-Filho et al., "Effects of 8-OH-DPAT on Sexual Behavior of Male Rats Castrated at Different Ages," Hormones and Behavior (1996) 30(3):251-258.

Rendell et al., "Sildenafil for Treatment of Erectile Dysfunction in Men with Diabetes a Randomized Controlled Trial," JAMA (1999) 281(5):421-426.

Sher et al., "Vaginal Sildenafil (Viagra): A Preliminary Report of a Novel Method to Improve Uterine Artery Blood Flow and Endometrial Development in Patients Undergoing IVF," Human Reproduction (2000) 15(4):805-809.

Shields et al., "Use of Sildenafil for Female Sexual Dysfunction," Ann. Pharmacother. (2006) 40:931-934.

Shifren et al., "Transdermal Testosterone Treatment in Women with Impaired Sexual Function after Oophorectomy," New England Journal of Medicine (2000) 343:682-688.

(56) References Cited

OTHER PUBLICATIONS

Singh et al. (2006) "Pharmokinetics of a Testosterone Gel in Healthy Postmenopausal Women," The Journal of Clinical Endocrinology & Metabolism 91(1):136-144.
Sipski et al., "Sildenafil effects on sexual and cardiovascular responses in women with spinal cord injury," Urology (2000) 55(6):812-815.
Spungen et al., "Treatment with an Anabolic Agent is Associated with Improvement in Respiratory Function in Persons with Tetraplegia: A Pilot Study," The Mount Sinai Journal of Medicine (1999) 66:201-205.
The Merck Manual of Diagnosis and Therapy 30-36 (Robert Berkow, M.D. et al. eds., Merck Research Laboratories, Merck & Co., Inc. 1992) (1997) (machine translation provided).
The RLS Encyclopedia of Drugs, RLS 2004, vol. 11 (machine translation provided).
Traish et al., "Female Genital Sexual Arousal: Biochemical Mediators and Potential Mechanisms of Dysfunction," Drug Discovery Today: Disease Mechanisms (2004) 1(1):91-97.
Tuiten et al., "Time Course of Effects of Testosterone Administration on Sexual Arousal in Women," Arch. Gen. Psychiatry (2000) 57:149-153.
Vidal's Handbook, Drugs in Russia, Moscow AstraPharmService 2001 (machine translation provided).
Written Opinion of the International Searching Authority for PCT/NL2007/050533, issued on May 5, 2009, 5 pages.
Adams et al., "Structure, function and pathophysiology of protease activated receptors," Pharmacology & Therapeutics (2011) 130:248-282.
Barry et al., "Novel Agonists and Antagonists for Human Protease Activated Receptor 2," J. Med. Chem. (2010) 53:7428-7440.
Forger et al., "Differential Effects of Testosterone Metabolites upon the Size of Sexually Dimorphic Motoneurons in Adulthood," Hormones and Behavior (1992) 26:204-213.
Regard et al., "Probing cell type-specific functions of Gi in vivo identifies GPCR regulators of insulin secretion," The Journal of Clinical Investigation (2007) 117(12):4034-4043.
Stewart et al., "Differential Effects of Testosterone Metabolites in the Neonatal Period on Open-Field Behavior and Lordosis in the Rat," Hormones and Behvaior (1979) 13:282-292.

PHARMACEUTICAL FORMULATIONS AND USES THEREOF IN THE TREATMENT OF FEMALE SEXUAL DYSFUNCTION

CROSS-REFERENCE TO RELATED APPLICATIONS

This application is a divisional of U.S. application Ser. No. 13/529,813 filed on 21 Jun. 2012, which is a divisional of U.S. application Ser. No. 11/595,778 filed 10 Nov. 2006, now U.S. Pat. No. 8,227,453 issued 24 Jul. 2012, which is a continuation of PCT application PCT/NL2005/000355 having an international filing date of 11 May 2005, which claims benefit of European patent application Nos. 04076402.9 filed 11 May 2004, 04078033.0 filed 4 Nov. 2004, 04078380.5 filed 13 Dec. 2004, 04078381.3 filed 13 Dec. 2004, and 04078455.5 filed 21 Dec. 2004. The contents of the above patent applications are incorporated by reference herein in their entirety.

TECHNICAL FIELD

The invention relates to the field of female sexual dysfunction. It specifically relates to the influence of the combination of testosterone or an analogue thereof and a PDE5 inhibitor (such as sildenafil, vardenafil or tadalafil) on sexual health in female subjects with Female Sexual Dysfunction (such as Female Sexual Arousal Disorder (FSAD) or Female Sexual Desire Disorder (FSDD)).

BACKGROUND ART

Female Sexual Dysfunction (FSD) refers to various disturbances or impairments of sexual function, including a lack of interest in sexual activity, repeated failure to attain or maintain sexual excitement, inability to attain an orgasm following sufficient arousal. A recent study estimated that 43% of women suffer from sexual dysfunction in the USA[1]. Low sexual desire (22% prevalence) and sexual arousal problems (14% prevalence) belong to the most common categories of sexual dysfunction of women. These categories are convenient in providing working definitions and an accepted lexicon for researchers and therapists. However, it may be incorrect to assume that these disorders are fully independent of each other. Both case studies and epidemiological studies demonstrate that these disorders can overlap and may be interdependent. In some cases, it may be possible to identify the primary disorder that led to the others, but in many cases, this may be impossible.

For the treatment of female sexual disorder a number of different treatments, with greater or lesser degrees of success have been suggested and applied. These treatments have either not been completely successful or the side effects are hardly acceptable. The present invention provides a new combination of therapeutic substances, given in a particular dosage scheme, which combination is effective and does not have serious side effects.

Thus the invention provides the use of a combination of a PDE5-inhibitor and testosterone or an analogue thereof, in the preparation of a medicament for the treatment of female sexual dysfunction. According to the invention, although it is not considered bound by theory, an effect on the central nervous system and the peripheral system are required, whereby the signal to the central system is provided by testosterone or an analogue thereof (having the same kind of activity) and the peripheral signal is provided by a PDE5-inhibitor. According to the invention the level of free testosterone should be a peak plasma level of free testosterone at least of about 0.010 nmol/L, which will typically occur about 20 minutes after administration of the testosterone. According to the invention, the effect of the peak plasma level of at least 0.010 nmol/l of free testosterone is to be reached at about the same time as the effect of the PDE-5 inhibitor. For an optimal effect it is desired that the peak effect of both compounds coincide. However, even if the peak effects only overlap partly, this still results in the desired effect (treatment of FSD). There is a time lag for the effect of testosterone (or the analogue) of about 3-6 (more specifically around 3-4.5) hours, in particular around 4 hours. PDE5-inhibitors such as vardenafil and sildenafil typically reach their peak plasma concentration (which should be at least 35 ng/ml for sildenafil, 2 μg/L for vardenafil and 40 μg/L for tadalafil) after about 1 hour after administration and thus the two pharmaceuticals are preferably presented as a kit of parts with instructions about the administration, or are packaged in one capsule or formula with differential release properties for the two compounds.

Testosterone in the circulation is typically bound by SHBG (steroid hormone binding globulin) and by albumin. It is important that the peak plasma level of testosterone as defined in the present invention is present and calculated as free testosterone, so a fraction not bound by albumin and SHBG. Thus the dose of testosterone given should be high enough to saturate the albumin and SHBG (i.e the concentration of testosterone must be high enough to overcome complete binding of testosterone by SHBG or albumin), or another way of avoiding binding to albumin or SHBG must be designed, such as the use of a competitor for the testosterone binding site on SHBG.

Testosterone is preferably given in a formulation wherein there is a short high peak in the blood circulation of the subject to which it is administered. The invention therefore provides a use, wherein the testosterone or an analogue thereof is provided in the form of a sublingual formulation, preferably a sublingual formulation comprising cyclodextrins as carrier. A typical example of such a formulation is given in hydroxypropyl-beta cyclodextrin, but other beta cyclodextrins and other usual excipients, diluents and the like are within the skill of the art for preparing a formulation comprising testosterone or an analogue thereof, which releases essentially all of the testosterone within one short burst. Said burst will typically be within a short time interval (for example within 60-120 seconds, more preferably within 60 seconds) upon administration, leading to blood peak levels of testosterone about 15-20 minutes later. In a preferred embodiment, the pharmaceutical is designed for sublingual administration and even more preferred said composition comprises cyclodextrin such as hydroxypropyl-beta cyclodextrin. A typical example of a prepared testosterone sample (for 0.5 mg of testosterone) consists of 0.5 mg testosterone, 5 mg hydroxypropyl-betacyclodextrines (carrier), 5 mg ethanol, and 5 ml water, but each of the amounts of these substances might be higher or lower.

Of course the pharmaceutical preparation comprising a PDE5-inhibitor should also be designed to give a peak plasma level at about the time when the testosterone effect is maximal. Such compositions are within the skill of the art, a typical example for oral administration is given in vardenafil HCl which is designated chemically as piperazine, 1-[[3-(1,4-dihydro-5-methyl-4-oxo-7-propylimidazo[5,1-f][1,2,4]triazin-2-yl)-4-ethoxyphenyl]sulfonyl]-4-ethyl-, monohydrochloride. In addition to the active ingredient, vardenafil HCl, each tablet contains microcrystalline cellulose, crospovidone, colloidal silicon dioxide, magnesium stearate, hypromellose, polyethylene glycol, titanium dioxide, yellow ferric oxide, and red ferric oxide. An other example is given in sildenafil citrate which is chemically designated as 1-[[3-(6,7-dihydro-1-methyl-7-oxo-3-propyl-1Hpyrazolo[4,3-d]pyrimidin-5-yl)-4-ethoxyphenyl]sulfonyl]-4-methylpiperazine citrate. In addition to the active ingredient, sildenafil citrate, each tablet contains the following ingredients: microcrystalline cellulose, anhydrous dibasic calcium phosphate, croscarmellose sodium, magnesium stearate, hydroxypropyl methylcellulose, titanium dioxide, lactose, triacetin, and FD & C Blue #2 aluminum lake. An other example is given in tadalafil which is chemically designated as pyrazino[1',2':1,6]pyrido[3,4-b]indole-1,4-dione,6-(1,3-benzodioxol-5-yl)-2,3,6,7,12,12a-hexahydro-2-methyl-,(6R,12aR)—. In addition to the active ingredient, tadalafil, each tablet contains the following ingredients: croscarmellose sodium, hydroxypropyl cellulose, hypromellose, iron oxide, lactose monohydrate, magnesium stearate, microcrystalline cellulose, sodium lauryl sulfate, talc, titanium dioxide, and triacetin.

It is clear, that preferably the (peak) effect of PDE5-inhibitor as well as the (peak) effect of testosterone coincide (completely). It is however noted that if the peak effect of testosterone and of the PDE5-inhibitor only partly overlap this still results in the desired effect. When the testosterone is provided such that it essentially releases all of the testosterone within one short burst to a female subject, the PDE5-inhibitor is preferably provided such that it results in a peak plasma concentration at least 3 hours after the administration of testosterone. Even more preferred, the PDE5-i effect is present 3.5-5.5 hours after the intake of testosterone. It is clear that the exact time of PDE5-inhibitor administration is dependent on the type of formulation used. If the PDE5-inhibitor formulation is released shortly after administration, it is of no use to provide it at the same time as the testosterone is provided, because there will be hardly any overlap of effect. If it takes some time before the PDE5-inhibitor is available from the used formulation, for example 3 to 4 hours, it can be/is administrated at the same time the testosterone is administrated.

For the present invention the routes of administration of choice are those which are the least invasive. Motivation for sexual behaviour should not be negatively influenced by invasive routes of administration. Because there is a time lag in the effect of testosterone, the two drugs necessary for a central effect and a peripheral effect cannot be administered at the same time (unless the administration of the PDE5-inhibitor is designed such that the drug is released after 3.5-5.5 hours after administration). The invention therefore provides a kit of parts comprising at least one pharmaceutical composition comprising testosterone or an analogue thereof and at least one pharmaceutical composition comprising a PDE5-inhibitor, whereby said composition comprising testosterone is designed to release all testosterone essentially immediately (for example within 60 seconds) at the target site. Said kit preferably contains instructions to use a pharmaceutical composition comprising testosterone 3.5-5.5 hours prior to sexual activity and a pharmaceutical composition comprising a PDE5-inhibitor 1-2 hours prior to sexual activity. The kit of parts may comprise a sublingual formulation of testosterone or an analogue thereof and a tablet or another formulation comprising a PDE5-inhibitor. The preferred PDE-5 inhibitors are sildenafil, vardenafil or tadalafil. The amount of testosterone per pharmaceutical composition comprising testosterone is at least 0.3 mg testosterone and at most 2.5 mg testosterone. Higher or lower doses may be necessary depending on the albumin and SHBG levels and the weight of the subject to be treated. The pharmaceutical composition comprising a PDE5-inhibitor comprises at least 25 mg sildenafil (or 5 mg vardenafil, or 5 mg tadalafil) and at most 100 mg sildenafil (or 20 mg vardenafil, or 20 mg tadalafil), or comparable dosages of other PDE5-inhibitors. Again these doses may vary with the weight of the patient. For the reasons already outlined above, a kit according to the invention may further comprise a compound capable of competing with testosterone or an analogue thereof for SHBG binding).

In a preferred embodiment, the testosterone analogue is a precursor or metabolite of testosterone. In case a precursor of testosterone is used, the kit further comprises instructions to (if necessary) increase the time period of 3.5-5.5 hours by adding the time which is needed to convert the precursor into testosterone. In case a metabolite of testosterone is used the time period of 3.5-5.5 hours is shortened.

In order to further enhance the effects of the kit of parts of the invention said kit may further comprise means for cognitive interventions and stimulation. Such information may be present on any data carrier (paper, CD, DVD), passive or interactive, or it may be a link to a website at least partially designed for the purpose of said cognitive stimulation. Sometimes it is preferred to present said cognitive stimulatory information subconsciously e.g. subliminally.

To further enhance the effects of the kit of the present invention a substance may be added to said kit which stimulates the mesolimbic dopaminergic pathway in the subject. This pathway is concerned with a relatively different kind of reward system which helps providing an increase in rewardseeking involved in sexual behaviour. Examples of such compounds are Apomorphine, a dopamine D2 agonist; Aripiprazol, a partial dopamine D2 agonist; Pergolide, a nonselectieve dopamine (DA) agonist; Pramipexole, a new dopamine receptor agonist with preference for D3 compared to D2 and D4 receptors; Bromocriptine, a nonselectieve dopamine (DA) agonist; Ropinirole hydrochloride, a non-ergoline dopamine agonist with a relatively high in vitro specificity and full intrinsic activity at the $D_2$ and $D_3$ dopamine receptor subtypes; it binds with higher affinity to $D_3$ than to $D_2$ or $D_4$ receptor subtypes; Roxindole, a potent (autoreceptor)-"selective" D3 dopamine agonist; Cabergoline, a dopamine D2 agonist; Lisuride, a nonselectieve dopamine (DA) agonist, and the autoreceptor antagonists; (+)-AJ 76, a D3-preferring, dopamine (DA) autoreceptor antagonist; (+)-UH232, a stimulant of dopaminergic transmission, which may preferentially antagonize autoreceptors of dopamine nerve terminals, as well as the reuptake blockers; Bupropion, an inhibitor of the neuronal uptake of norepinephrine, serotonin and dopamine; Amineptine, a (relatively) selective dopamine reuptake inhibitor; GBR 12909 (vanoxerine), a dopamine reuptake inhibitor; and Amantadine; a NMDA receptor antagonist and dopamine reuptake inhibitor.

To further enhance the effects of the kit of the present invention a substance is (optionally) added which inhibits the central and peripheral adrenergic tone, i.e. inhibits or dampens central and peripheral extracellular norepinephrine concentrations. Activation of alpha 2-receptors located in the central nervous system results in inhibition of sympathetic tone. Examples of such compounds are clonidine, an alpha 2 agonist; imidazoline, a partial alpha 2 agonist; and dexmedetomidine, an alpha 2 agonist.

The kit of parts is useful for any individual suffering from any form of FSD, be it through psychological or physiological causes or combinations thereof. It is thus also useful for subjects having FSD because of other medicines and/or drugs—such as SSRI's—; subjects suffering from hypogonadism, etcetera.

Low sexual desire, sexual arousal problems and hampered orgasm are candidates for psychopharmacological treatment. These categories of sexual problems are also linked to three (transitional and overlapping) phases of the human sexual response (sexual desire, sexual arousal and orgasm), which are regulated by relatively independent neurotransmitter functions. Traditionally, motivated behaviours have been divided into appetitive and consummatory components. Activities aimed at obtaining reward and satisfaction belong to the appetitive component. The fundamental appetitive motivational process is an intrinsic brain function, and is especially related to the predictive value of stimuli for reward. Processing of motivationally relevant information (i.e. stimuli predicting reward) causes an increase in activity of the meso-accumbens dopaminergic (DA) system (i.e. DA neurons of the ventral tegmental area (VTA) innervating the nucleus accumbens (NAS)), a component of the mesolimbic dopamine system. The activity of this system is increased during flexible approach behaviour when anticipating reward related to copulation[2]. Increasing activity in these dopaminergic pathways facilitates sexual motivation, in particular anticipatory sexual behavior[3]. Aripiprazole is, among others, an example of a drug which influences dopaminergic pathways, and which may be used in combination with testosterone or an analogue thereof and a PDE5-inhibitor to affect sexual motivation and behaviour. Aripiprazol is a high-affinity partial agonist of the dopamine D2 receptor and serotonin 5-HT1a receptor, and antagonist of the 5-HT2a receptor. Aripiprazol is described as a dopamine system stabilizer which is due to its partial agonistic actions at the D2 receptor, especially the presynaptic D2 receptors, for which it has higher affinity. Stimulation of autoreceptors located on dopamine nerve terminals results in an inhibition of dopamine synthesis and release. Thus, in a low dopaminergic state of the meso-accumbens DA system, aripiprazol would antagonize presynaptic D2 receptors, freeing the NAS-projecting DA nuclei in the VTA from autoinhibition. The medial prefrontal cortex (mPFC) mediates behavioural inhibition. Dopamine in the mPFC plays an important role in behavioural inhibition. Illustrative of mPFC-DA's inhibitory role is the inhibition of the meso-accumbens DA system; high extracellular concentrations of mPFC-DA inhibit meso-accumbal DA activity, and low extracellular concentrations of mPFC-DA activate meso-accumbal DA activity through disinhibition. It is therefore conceivable that a dopaminergic role in FSD is not restricted to meso-accumbal DA, but extendable to mPFC-DA, where symptoms of FSD are enhanced with high activity of mPFC-DA, albeit via inhibition of accumbal DA or via inhibition of other cognitive or emotional factors involved in FSAD. The partial agonistic action of aripiprazol will then have a positive effect on alleviation of FSD (symptomatology) through agonism of presynaptic D2 receptor in the mPFC, thereby inhibiting DA release in this area. Anticipating sexual reward will produce arousal of the genitalia, in which at least three key neurotransmitters are involved: acetylcholine, norepinephrine and nitric oxide. Acetylcholine and nitric oxide both promote erections in men and lubrication and swelling in women. Norepinephrine inhibits erections in men and lubrication and swelling in women. Orgasm, the consummatory phase of human sexual response is facilitated by descending spinal noradrenergic fibers and innervation of the genitalia, and inhibited by descending spinal serotonergic fibers.

Testosterone in Women

In many mammalian species, female sex steroids are necessary for the expression of female sexual behavior. As a result the capability for copulation in these animals is limited to the period of ovulation[4,5]. Higher primates—like humans—show sexual intercourse outside the periovulatory period. For these animals it has been suggested that testosterone is involved in female sexual behavior[6]. The disappearance of testosterone following ovariectomy and adrenalectomy is accompanied by a complete loss of libido[7,8], while substitution of this steroid maintains sexual desire and fantasies after surgical menopause[9].

Testosterone, Exposure to Sexual Cues and Vaginal Arousal in Normal Women

An important aspect of sexual motivation is physiological sexual responding. Measured as an increase in vaginal vasocongestion elicited by sexual stimuli, this responding is considered to be preparatory for copulatory behavior[10]. In hypogonadotropic hypogonadal females we found that substitution with testosterone undecanoate 40 mg orally per day during an 8-week period enhanced vaginal responsiveness[10]. This effect was not found in another group of hypogonadotropic hypogonadal patients (unpublished data). In both studies subjects received testosterone each morning, but patients in the first experiment were tested in the afternoon and patients in the second experiment in the morning. The different outcomes on physiological responding between these experiments may be caused by a time dependent effect of testosterone on vaginal arousal. In a third experiment, we examined whether administration of a single dosage of testosterone sublingually, as compared with a placebo, increases vasocongestion during presentation of visual erotic stimuli[11]. On treatment days we exposed eight sexually functional women with intervals of an hour and a half, to six erotic films depicting intercourse. The intake of testosterone caused a sharp increase in plasma levels of testosterone of short duration. About three to four and a half hours after this testosterone peak, we found a striking increase in vaginal responsiveness when the subjects were exposed to the visual sexual stimuli (see also FIG. 1). These findings demonstrate a time lag in the effect of sublingually administered testosterone on genital arousal in sexually functional women.

The results of the above mentioned studies demonstrate that testosterone is involved in female sexual motivation in a time dependent fashion. The influence of sex steroids on sexual behavior might be explained by a steroid-responsive neural network, a highly interconnected group of sex hormone receptor-containing neurons in the brain[12]. This network is not a closed circuit, but serves reproductive aims by functioning as an integrating and activating center between external sensory cues, hormonal processes and reproductive behavior. This is partly accomplished by selective filtering of sensory input and amplification of signals that may facilitate sexual behavior. We assume that an increase in vaginal vasocongestion induced by sexual stimuli is preparatory for copulatory behavior. Visual exposure to sexual intercourse between members of the species of the onlooker is a potent releasing stimulus for such a preparatory motivational response. Both men and women have a marked capacity to respond to erotic films with a genital response[13]. The increased motivational sensitivity for sexual cues induced by testosterone is presumably the result from an altered brain state, in which dopaminergic, serotonergic and noradrenergic pathways are involved. This altered state might also be sensitive to internal cues as evoked by sexual fantasy.

In another experiment we demonstrated that attention directed at alterations in genital arousal produced concordance between physiological and subjective indices of sexual arousal[14]. There are reciprocal relationships between sexual desire, sexual arousal and the ability and potency of orgasm. A reduced sexual desire will affect sexual arousal and visa versa; both indices of sexual function might influence orgasm potency and visa versa.

Phosphodiesterase 5 Inhibitors and Sexual Arousal

In several studies it has been shown that selective type 5 phosphodiesterase (PDE5) inhibitors improve erectile function in men with erectile dysfunction, on average close to normal function[15]. In the penis, nitric oxide (NO) released from nerves and endothelium, induces production of cyclic guanosine monophosphate (cGMP). cGMP is a key mechanism in relaxing smooth muscle, necessary for the induction of an erection. This nucleotide is hydrolyzed by the phosphodiesterases, from which the main activity in the corpora cavernosa is due to PDE5. Therefore, during sexual stimulation the action of NO/cGMP on erectile function will be enhanced by PDE5-inhibitors[16]. The genitalia of both sexes have common embryological origins. Recently, it has been shown that the clitoris consists of an erectile tissue complex, which embeds the anterior vaginal wall. Clitoral erection and the anterior wall of the vagina are highly involved in female sexual arousal and response. It has recently been shown that sildenafil—a PDE5-inhibitor—improves sexual performance in sexual functional women.[17]

Although in both men and women similar specialized vascular mechanism are involved in the genital response, an increase in Vaginal Pulse Amplitude (VPA) cannot be considered to be the equivalent of an erection. A necessary but not sufficient condition for an erection is dilatation of arteries and resulting increased blood inflow. In the penis there are corpora (corpus cavernosa (two) and corpus spongiosum (one)) containing small irregular compartments (vascular spaces). The smooth muscles in the cavernous sinusoidal walls are normally tonically constricted under the control of an active sympathetic (adrenergic) tone. Relaxation of cavernous smooth muscle of the corpora results in filling and enlargements of the compartments with blood, which will be accompanied by an erection. Although the precise mechanisms are unknown, sympathetic innervations and Nitric Oxide are believed to be both principal mediators in relaxation of the corporeal smooth muscles. In the penis, sympathetic innervations of the blood vessels are sparse, while the smooth muscles are richly innervated by this system. In contrast, the blood vessels of the penis are richly innervated by the parasympathetic system, while innervations of the smooth muscles by this system are sparse. Consequently, there are relatively independent effects of these two parts of the peripheral nervous system on processes involved in the occurrence of an erection. Initiation of dilatation of the penile arteries and subsequent increase of blood flow to the cavernous tissue is regulated by the parasympathetic nervous system (initiation of an increase in this cholinergic activity depends on signals by the brain). However, without relaxation of the smooth muscles there will be no erection. Reduction of the sympathetic tone and consequent relaxation of smooth muscles appears to be a relative independent prerequisite for the initiation of an erection. Thus, penile erection occurs in response to increased activity of the sacral parasympathetic innervations and a decreased activity of sympathetic pathways. In the penis, nitric oxide (NO) released from nerves and endothelium, induces production of cyclic guanosine monophosphate (cGMP). cGMP is a key mechanism in relaxing smooth muscle, necessary for the induction of an erection. The production and release of NO might be influenced by a decrease in activity of the sympathetic branch.

Brain Activity Mediates the Influence of Psychosocial Circumstances on Sexual Behaviour and Sexual Feelings Via Inhibitory and Excitatory Regulating Mechanism The prefrontal cortices of the human brain are crucial for cognitive functions involved in planning, execution and control of behaviour. An important aspect of these cognitive functions is inhibition of limbic system induced emotional responses, such as sexual behaviour. Psychological processes are also involved in three distinct (transitional and overlapping) phases of the human sexual response, as well as disturbances in these phases leading to low sexual desire, sexual arousal problems and hampered orgasm. Thus, an increase in activity of the prefrontal cortex associated with inhibition might reduce sexual desire, sexual arousal and orgasm capacity. Activity in the prefrontal cortices is also involved in the regulation of the sympathetic and parasympathetic branches of the peripheral nervous system. An increase in prefrontal activity is accompanied by a decrease in parasympathetic activity and an increase in sympathetic activity. Alterations in these branches occur asymmetrically. Moreover, the sympathetic branch of the peripheral nervous system seems to be more sensitive to psychogenic induced alterations. Thus psychological processes controlled by the prefrontal cortices appear to be directly involved in the physiological mechanisms regulating induction of an erection. It might be assumed that the same physiological mechanisms are regulating the different components of the female sexual response (i.e. parasympathetic innervations are regulatory for the VPA, and sympathetic innervations are, together with Nitric oxide, responsible for swelling and lubrication).

In a recently conducted experiment (not published) in healthy sexual functional women, we used a delayed measurement design in which subjects ingested one dosage of testosterone (0.5 mg sublingual) or placebo and after 4 hours underwent fMRI while watching neutral and erotic videos. Hereafter subjects were conducted to a laboratory where their VPA in response to neutral and erotic videos was measured. As expected, in the placebo condition we found activation of cortical and subcortical structures and deactivation of dorsal prefrontal areas comparable to other imaging studies on brain activation in response to erotic stimulation. Because of testosterone delayed effect on enhancing VPA, we expected enhancement of these 'erotic' structures in this fMRI study. However, the opposite is true. Women on testosterone, show a decreased activation of all brain structures during erotic exposure implicated in the normal sexual response. Furthermore, 2 structures showed a very significant increase: the septum, which functions as a restrainer of emotional overshoot, and the left dorsolateral PFC, which functions as inhibitor of automated/reflexive responses. As stated, usually deactivation of dorsal prefrontal areas is observed.

Depending on circumstances and individual differences, testosterone can produce effects that deviate from the expectations one would have given the functional role of testosterone in the regulation of sexual behaviour. This inhibition of the centrally regulated autonomous sexual response was also apparent in the relative change in the VPA. Contrary to the expectations the VPA was smaller in the testosterone condition as compared with placebo, and probably the result of a continuing inhibition mechanism induced during the fMRI procedure.

The Synergistic Effect of a Combination of Testosterone and PDE-5 Inhibitor on Vaginal Arousal in Women Suffering from Female Sexual Disorder In a recently conducted experiment (see experimental part) in women suffering from Female Sexual Dysfunction, we found at different time intervals no effect from one dosage of testosterone, nor from a PDE5-inhibitor—as compared with a placebo—on vaginal arousability, nor on sexual desire and genital sensations. In this experiment we found, however, that one dosage of testosterone (0.5 mg sublingual) combined with the administration of a PDE5-inhibitor (dosed in a way such that T max arises about 3.5-5.5 hours after the free testosterone peak) caused four hours after the plasma testosterone peak a significant higher Vaginal Pulse Amplitude during exposure to erotic stimuli. This effect was less pronounced in a subgroup of women who were sexually abused during their childhood. We found no effect on sexual desire and on subjective sexual arousal. Treatment with testosterone as well as the combination of testosterone and a PDE 5 inhibitor caused an increase in attentional engagement (or withdrawal) for sexual cues, as compared with placebo and/or a PDE5-inhibitor. Attentional engagement is an important function for normal human sexuality. Testosterone combined with a PDE5-inhibitor produced a statistically significant increase in genital arousal.

In one of its embodiments, the invention provides the use of a combination of a PDE5-inhibitor and testosterone or an analogue thereof, in the preparation of a medicament for the treatment of female sexual dysfunction.

Testosterone is also known under the chemical name 17-β-hydroxyandrost-4-en-3-one which can be obtained in various ways: it may be isolated and purified from nature or synthetically produced by any manner. The term "or an analogue thereof" includes any useful metabolite or precursor of testosterone, for example the metabolite dihydrotestosterone. It is clear to the skilled person that if a metabolite or precursor of testosterone is used, the time point for administration of a PDE-5 inhibitor probably needs to be adapted. If, for example, dihydrotestosterone is used, the time of administration of the PDE5-inhibitor lies approximately half an hour earlier (as this is the approximate time it takes for excess testosterone to be converted to dihydrotestosterone). The amount of PDE5-inhibitors is still expanding and non-limiting examples are the following: GF-196960/IC351 (tadalafil), Bay-38-9456 (vardenafil), UK-103320 (Sildenafil), E-4021, E-8010, E-4010, AWD-12-217 (zaprinast), AWD 12-210, UK-343,664, UK-369003, UK-357903, BMS-341400, BMS-223131, FR226807, FR-229934, EMR-6203, Sch-51866, IC485, TA-1790, DA-8159, NCX-911 or KS-505a. Other examples can be found in WO 96/26940.

Preferably, the PDE5-inhibitor is provided at least 3 hours after the administration of the testosterone, even more preferably such that $C_{max}$ arises about 3.5 to 5.5 hours after the plasma free testosterone peak. As already described above and depending on the formulation, the PDE5-inhibitor can also be given at the same time testosterone is administrated.

Conditioning of Positive Associations Between Different Modalities of the Sexual Response Treatments with a dosage of testosterone combined with a PDE5-inhibitor produce alterations in brain and bodily functions which will make learning of positive associations between sexual stimuli, genital arousal and subjective experience possible. Moreover, the treatment of FSD with a combination of testosterone and a PDE5-inhibitor is preferably augmented by an "approach induction" treatment. To create a more permanent psychological change, the central bodily processes activated by testosterone and a PDE5-inhibitor under sexually relevant stimulation need to be perceived and need to become associated with a positive hedonic tone or with activation of the behavioral approach system. The perception of bodily reactions by focusing attention on genital arousal is made possible by testosterone (whereby the genital arousal is synergistically enhanced by the PDE5-inhibitor) and can be emphasized by verbal instructions. A positive hedonic tone cannot be taken for granted in the population of FSD patients. In order to achieve a positive tone, patients can be exposed to positive stimuli during the effective phase of the drugs (that is, at least 3 hours after testosterone intake). These positively motivated stimuli consist of pictures of happy faces of persons of the patient's sexually preferred gender, possibly including the face of the partner. The pictures of the faces are presented subliminally, so that in an unobtrusive way the behavioral approach system becomes activated.

The treatment of FSD might consist of creating a situation in which the patient learns to associate genital arousal with a positive hedonic tone or activation of the behavioral approach system. This requires inducement of genital arousal (by sexual stimuli and a PDE5-inhibitor), sustained attention to sexual stimuli and to genital arousal (made possible by testosterone) and activation of the behavioral approach system (by subliminal presentation of pictures of happy faces).

The invention further provides a method for treating a female suffering from female sexual dysfunction by providing to said female a combination of a PDE5-inhibitor and testosterone or an analogue thereof.

The invention will be explained in more detail in the following, non-limiting example.

EXAMPLES

Participants

Fourteen women with a heterosexual orientation (Mean age: 40.6 years; sd: 10.4; premenopausal n=8, postmenopausal n=6) who have been experiencing FSD (i.e. low sexual desire, low sexual arousal or decreased orgasm potency) for at least six months prior to study entry participated in this study. Subjects in fertile age used contraceptives (UID's, sterilization, oral contraceptives, except contraceptives containing anti-androgens). A pregnancy test was part of the procedure. Subjects were interviewed and examined by a gynecologist to exclude pregnancy or breast feeding, vaginal infections, major operations to the vagina and/or vulva or unexplained gynecological complaints. Participants did not have a history of endocrinological, neurological of psychiatric treatment. Cardiovascular condition was tested and ECG was checked for significant abnormalities. Standard blood chemistry and hematology tests were performed. Participants did not abuse drugs and were required not to use alcohol or psychoactive drugs the evening before and the day of experimentation. Subjects could not make appointments during their period of menstruation.

Procedures

This study was approved by the Dutch medical-ethical committee (STEGMETC). The experimental trials were preceded by a screening visit. At this screening visit subjects were interviewed by a psychologist/gynecologist to diagnose for FSD and to determine eligibility for study participation. Weight, height, blood pressure (supine and standing), heart rate, respiration rate, and body temperature were measured. A supine, 12-lead ECG was recorded and examined by a physician (and when necessary, a cardiologist). A gynecological examination and urine pregnancy test were performed. Cultures were taken to exclude *Chlamydia* or *Gonococcus* infections.

Eligible subjects underwent a familiarization trial following the screening. A trained female experimenter familiarized the subject with study requirements and procedures. This included the use of the vaginal photoplethysmograph (a tampon-shaped device). The subjects viewed during 5 minutes a neutral film fragment followed by an erotic film fragments of 5 minutes. Hereafter they practiced on a shortened version of the emotional Stroop task.

For the experimental trials we used a double blind randomly assigned placebo controlled cross-over design with four drug conditions:
1) Placebo
2) PDE5-inhibitor
3) Testosterone (0.5 mg sublingual)
4) testosterone+PDE5-inhibitor (the two compounds were given at the same time, but the PDE5-inhibitor was dosed/formulated such that the effect of the testosterone and the effect of the PDE 5-inhibitor at least partly overlapped) Each subject underwent the four different drug treatments (i.e. PDE5i, testosterone, PDE5i+testosterone and placebo) at four separate experimental days. The four experimental days were separated by (at least) a three-day period.

During each day of drug manipulation subjects underwent the following measurements:
−1:00 hrs: Emotional Stroop Task
−0:15 hrs: Trial 1
0:00 hrs: Intake drugs
0:05 hrs: Trial 2
2:45 hrs: Trial 3
4:15 hrs: Trial 4

Each day started with a physical examination (measurements of vital signs, blood pressure, heart rate, temperature and respiration rate). Blood samples (8 ml) were taken for hormone analyses. Subjects then were seated in the sound attenuated, dimly lit experimental room. In order to make this room less "sterile" geographic posters were hung on the walls and an air perfumer was placed behind the subjects. The subjects then executed the emotional Stroop task (15 minutes). The experimenter brought the vaginal probe and the subject was left alone in the room to insert the probe. The subject was instructed to sit as quietly as possible while viewing the film fragments. A 10 minute neutral fragment was followed by a 5 minute erotic film fragment. After these baseline measurements, the subjects took medication: testosterone (0.5 mg; or placebo) sublingually, with cyclodextrines as carrier and Vardenafil (10 mg, or placebo) hidden in a capsule. The medication was followed by another set of neutral (5 minutes) and erotic (5 minutes) film fragments. The subjects removed the vaginal probe, and were taken to a waiting room for a pause of 2 hours. During this pause they could consume their lunch. Coffee and tea were unlimited available. This pause was followed by a third set of neutral (5 minutes) and erotic (5 minutes) film fragments. Again subjects had to wait for 2 hours, so that the last VPA measurement was taken 4 hours after medication. This last film-trial (neutral, erotic film fragments) was followed by a second presentation of the emotional Stroop. The experimental day ended with a short physical examination including drawing of a blood sample (8 ml for hormone analyses) and collection of AE and SAE.

Emotional Stroop Task:

An unmasked and a masked version of the Emotional Stroop Task comparing colour-naming latencies on neutral and erotic words were used. In both the unmasked and the masked condition eight erotic and neutral words are presented in different colours (i.e. red, green, blue and yellow). An extra set of stimuli consisting of letter strings was used for practice trials. Subjects were instructed to ignore the content of the words and to name the colour of the words as quickly as possible (in the masked condition, the colour of the mask has to be named). Each trial consisted of a fixation point which is shown for 750 ms, followed by the target stimulus (the coloured neutral or erotic word). In the masked condition the word picture is presented for about 24 ms and then masked by randomly cut, reassembled letters in the same colour. A microphone connected to a voice-level detector was placed in front of the subject. Initiation of vocal response was registered by the computer's clock and terminated the target presentation (with a no-response maximum of 3000 ms). Thirty-two neutral words and thirty-two erotic words were presented blocked. The same words were used for each test, however, the sequence of words and colours differed all 8 times this task was used.

Results

VPA Measurements

During the testosterone condition, one subject became nauseated watching the erotic film and decided not to participate further that day. For the psychophysiological evaluation the VPA (Vaginal Pulse Amplitude) is used. The VPA reflects phasic changes in the blood volume corresponding with each heartbeat; higher levels indicate higher levels of blood flow. The dependent variable used is the amplitude of the pulse wave. Before the mean VPA was calculated, the raw signal (sample rate was 20 Hz) was digitally bandpass filtered with a butterworth filter (−3 dB cutoff frequency range 0.7-1.5 Hz; 40 dB down/octave). Movement artefacts were detected by visual inspection of the signal and removed manually. Hereafter the amplitude was measured as the distance between the top and bottom of a pulse wave. The mean VPA was calculated as the average of these amplitudes across 30 s periods.

The magnitude of the VPA response also depends on the exact placement of the probe. In order to compare conditions, it is not meaningful to examine the absolute mean amplitude values in the neutral or erotic conditions. Instead, we use the mean change in amplitude from neutral to erotic film fragment divided by mean score in the neutral condition during each film trial as endpoint in the analyses.

Figure 1:
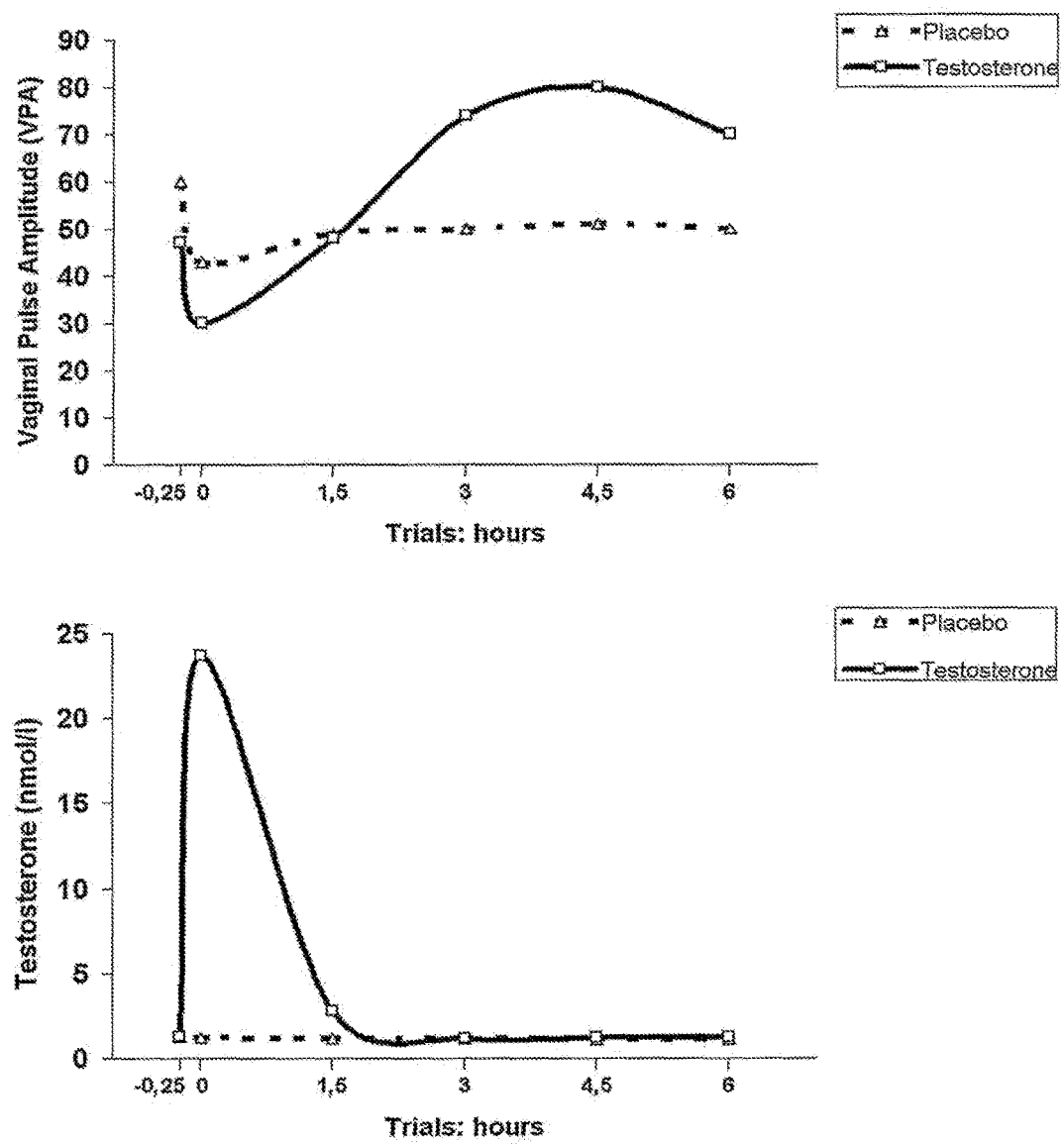
Figure 2:
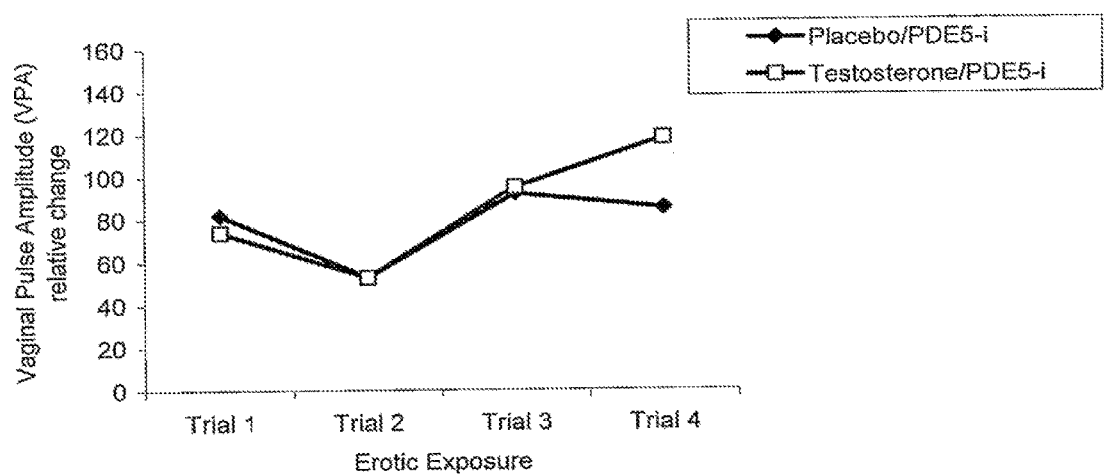
FIG. 2 shows the effect of the pharmaceutical preparation according to the invention (P<0.035) as compared with a placebo/PDE5-inhibitor on VPA in women suffering from FSD.
Figure 3:
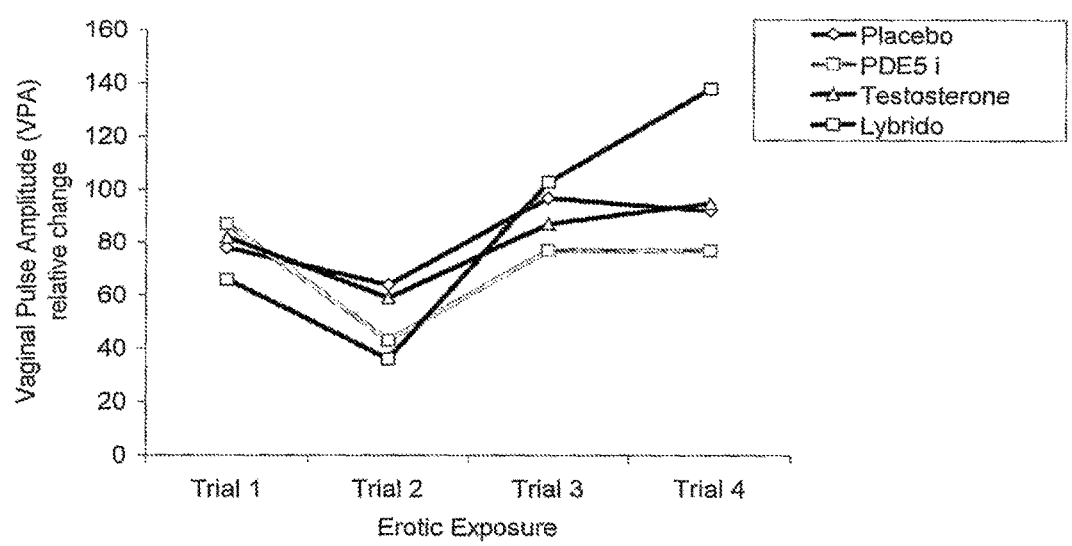
FIG. 3 shows the effect of the pharmaceutical preparation according to the invention (P<0.04) as compared with a placebo, a PDE5-inhibitor and testosterone in women suffering from FSD.
Figure 4:
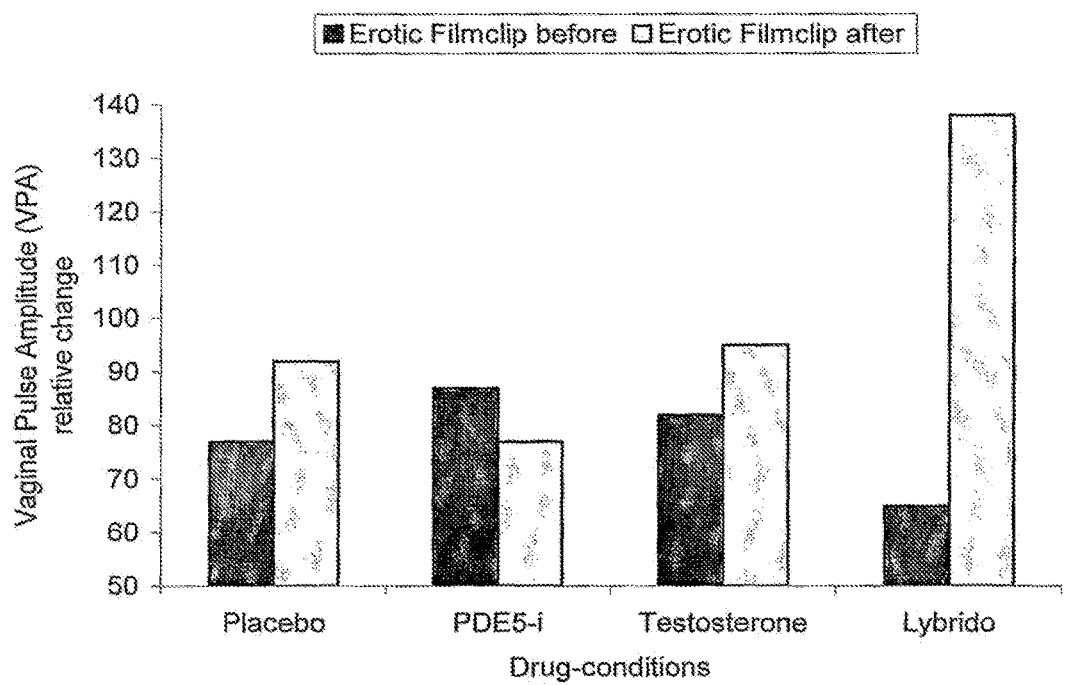

The resulting difference scores were subjected to a 2 Steroid (testosterone yes/no)×2 PDE5i (vardenafil yes/no)×2 before-after (trial 1 versus trial 4) repeated measures ANOVA. An interaction effect was found for the steroid condition over trials ($F(1.12)=5.75$; $p<0.04$) implicating that the increase from before to after measurement was significantly higher for drug conditions containing the steroid (testosterone+placebo and testosterone+Vardenafil) than for the drug conditions without the steroid (placebo+placebo and placebo+Vardenafil). Further analyses of the before medication (trial 1) versus after medication (trial 4) responses showed that the increase in VPA between neutral and erotic films was not significant in the placebo condition nor in the Vardenfil or testosterone condition (see also FIG. 4). Only the combined treatment condition (Vardenfil+testosterone) lead to a statistically significant increase in VPA before compared with after medication (F(1.12)=3.229; p=0.007).

We hypothesized the effects of sexual stimulation and medication on genital responses to be associated with changes in central mechanisms. To test for associations with changes in attentional processes we used the StroopRT as measurement point. StroopRT is the difference in mean reaction times on colour naming of the neutral and the sexual words.

During visual inspection of the data, we found two subgroups within our sample: a group of women who were sexually abused during childhood and a group of women who did not report such abuse. We decided to include sexual abuse during childhood as a between subjects variable in the analyses.

Figure 5:
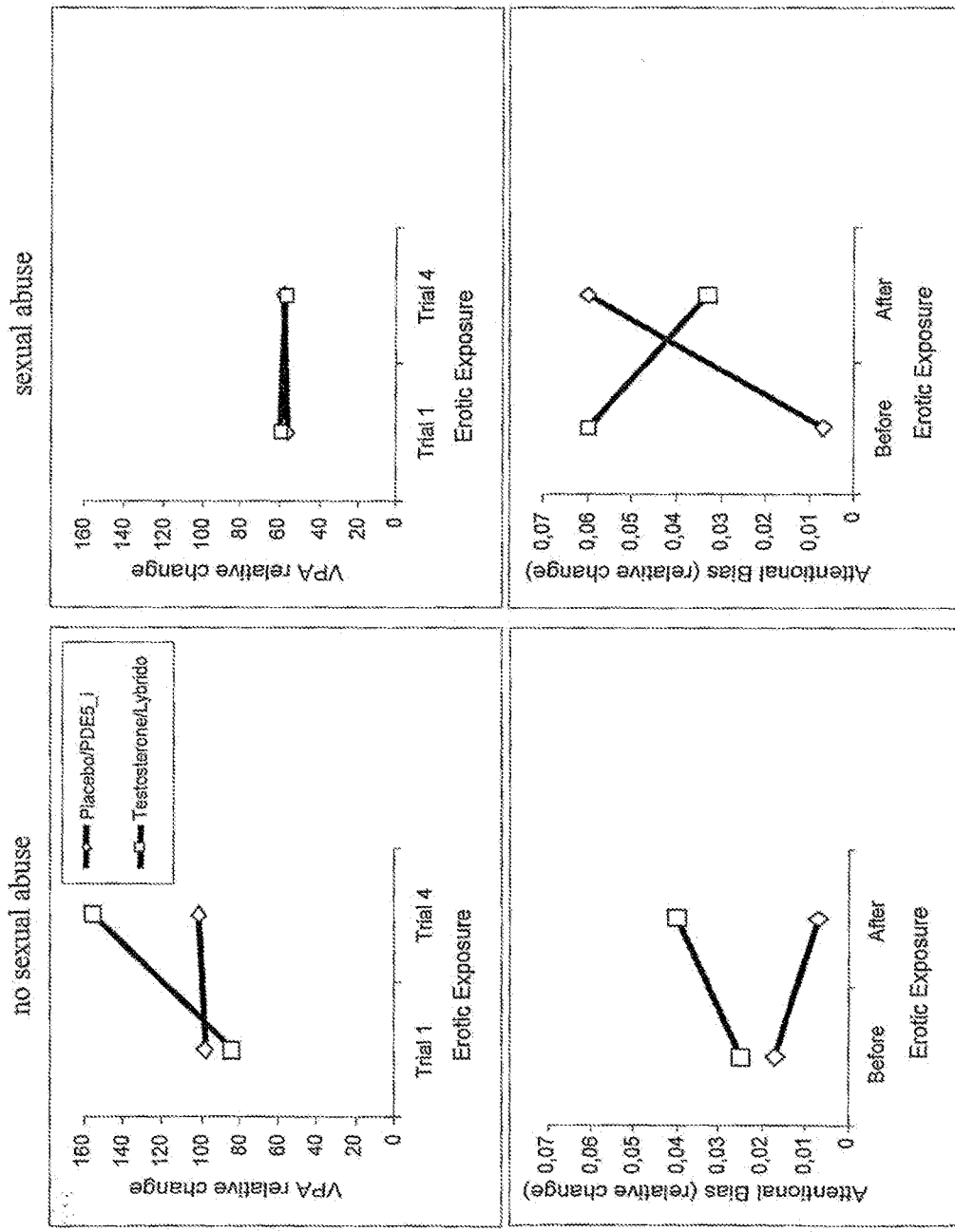

In the unmasked condition no statistically significant results were found. Analyses reported heretoforeward reflect results in the masked condition of the Stroop task. The MANOVA revealed a significant interaction between Steroid, Trial and Sexual-abuse-in-childhood (F(2.10)=13.6; p=0.001). Within-subjects contrasts confirmed significant effects for both VPA (F(1.11)=10.97; p=0.007) and StroopRT (F(1.11)=5.85; p=0.034) (FIG. 5).

Subjects who have been sexually abused during childhood show an attenuated VPA to erotic stimuli (before medication increase in VPA during erotic film relative to neutral film is <60%, compared to >90% increase for not-abused subjects) and no increase over trials with or without testosterone. However, these subjects are not insensitive to testosterone. Under influence of testosterone they develop an attentional bias away from sexual stimuli (StroopRT increases). Not-abused subjects show an opposite pattern: their attention for sexual stimuli increases (StroopRT decreases) and parallel their VPA response to the erotic film increases in the testosterone versus no-testosterone conditions. (Univariate analyses: VPA: 2 Steroid (testosterone yes/no)×2 Trial (before–after medication) ANOVA with VPA as within subjects dependent measure and sexual abuse as between subjects factor: F(2.10)=5.9; p=<0.035; StroopRT: 2 Steroid (testosterone yes/no)×2 Trial (before-after) ANOVA with StroopRT as dependent measure and sexual abuse as between subjects factor: F(2.10)=4.2; p<0.07).

In this group of women suffering from FSD, Vardenafil did not lead to a significant difference in VPA under condition of sexual stimulation compared to placebo. Apparently, peripheral manipulations are not sufficient and central mechanisms need to be influenced. We show that testosterone is such a centrally acting influence on sexual mechanisms. However, for our subjects, testosterone alone was not sufficient for a significant increase in VPA compared to placebo. Only the combination of testosterone and Vardenafil lead to a significant increase in VPA compared with placebo.

We found that we could distinguish subgroups of subjects. For a subgroup of sexually abused women testosterone had an effect on attention for sexual stimuli. When these subjects had a greater attention for sexual stimuli their genital response did not increase. Both healthy women and women with FSD who are not abused respond with a genital reaction when their attention is directed to sexual stimuli. We showed in this study that for patient without a history of abuse, the combination of testosterone and a PDE5-inhibitor is beneficial in that it increases both resources allocated to the processing of sexual stimuli as well as their genital response to these sexual stimuli.

The observed effect was less pronounced in a subgroup of women who were sexually abused during their childhood. For these women, the testosterone or an analogue thereof and a PDE5-inhibitor is optionally complemented with psychotherapeutic intervention.

In a small study (N=4) we further investigated the efficacy of subliminal presentation of faces of happy men during erotic film clips in 4 healthy women, following administration of the testosterone and PDE5-inhibitor combination. Women reported increased subjective sexual arousal in the subliminal happy male face presentation condition, in comparison to erotic film excerpts only condition.

FIGURES

FIG. 1

Graphs depicting a delay between testosterone administration and VPA in healthy subjects

FIG. 2

Results of VPA measurement in women suffering from FSD receiving a placebo combined with a PDE-5 inhibitor or the pharmaceutical preparation according to the present invention comprising testosterone and a PDE-5 inhibitor (this last combination is also called "Lybrido").

FIG. 3

Results of VPA measurement in women suffering from FSD receiving a placebo, and PDE-5 inhibitor, testosterone or the pharmaceutical preparation according to the present invention.

FIG. 4

VPA measurements of different treatments

FIG. 5

Sexual abuse, attentional bias and VPA.

REFERENCES

1. Laumann, E. O., Paik. A. and Rosen, R. C.: Sexual dysfunction in the United States: prevalence and predictors. JAMA 10: 281, 537, 1999.
2. Ikemoto, S. & Panksepp J. The role of nucleus accumbens dopamine in motivated behavior: a unifying interpretation with special reference to reward-seeking. Br Res Rev 31: 6-41, 1999.
3. Melis, M. R. & Argiolis, A. Dopamine and sexual behavior. Neurosc. Biobehavioural Reviews 19: 19-38, 1995.
4. McCarthy M M, Albrecht E D. Steroid regulation of sexual behavior. Trends Endocrinol Metab. 1996; 7:324-327.
5. Pfaff D W, Schwatz-Giblin S, McCarthy M M, Kowl L-M. Cellular and molecular mechanisms of female reproductive behaviors. In: Knobil E, Neill J D, eds. The Physiology of Reproduction, 2nd ed, vol 2. New York, N.Y.: Raven Press; 1994: 107-220.
6. Freeman L M, Rissman E F. Neural aromatization and the control of sexual behavior. Trends Endocrinol Metab. 1996; 7:334-337.
7. Waxenberg S E, Drellich M G, Sutherland A M. Changes in female sexuality after adrenalectomy. J Clin End Metab. 1959; 19:193-202.
8. Drellich M G, Waxenberg S E. Erotic and affectional components of female sexuality. In: Masserman J, ed. Science and psycho-analysis. New York: Grune and Stratton, 1966.
9. Sherwin B B, Gelfland M M & Brender W: Androgens enhances sexual motivation in females: a prospective, cross-over study of sex steroid administration in the surgical menopause. Psychosomatic Medicine, 49, 397, 1985.

10. Tuiten A, Laan E, Panhuysen G, Everaerd W, de Haan E, Koppeshaar H & Vroon P: Discrepancies between genital responses and subjective sexual function during testosteron substitution in women with hypothalamic amenorrhea. Psychosomatic Medicine, 58, 234, 1996.
11. Tuiten A, van Honk J, Koppeschaar H, Bernaards C, Thijssen J & Verbaten R: Time course of effects of testosterone administration on sexual arousal in women. Archives of General Psychiatry, 2000, 57, 149-154.
12. Cottingham S L, Pfaff D. Interconnectedness of steroid hormone-binding neurons: existence and implications. Curr Topics Neuroendocrinol 1986; 7:223-249.
13. Bancroft, J. Human Sexuality and its Problems (Churchill Livingstone, Edinburg London Melbourne and New York, 1989).
14. Tuiten A, van Honk J, Verbaten R, Laan E, Everaerd W, Stam H. Can Subliminal Testosterone increase subjective and physiological measures of laboratory-induced sexual arousal? Archives of General Psychiatry, 2002, 59, 465-466.
15. Potempa, A J., Bernard I., and Ulbrich E. Under Flexible dosing, "Real world" condition PDE5 inhibitor improved erectile function in a broad population of men. Europ Urol Suppl. 2: 96, 2003. Klotz T., Sashe R., Heidrich A., et al. PDE5 inhibitor increases penile rigidity and tumescence in erectile dysfunction patients: a Rigiscan and pharmacokinetic study. World J Urol 19: 32-39.

The invention claimed is:

1. A method of treating a sexual disorder in a female, said method comprising:
   administering to a female suffering from said sexual disorder a combination of a PDE5-inhibitor and testosterone or an analog thereof, so as to treat the sexual disorder,
   wherein said analog of testosterone is a precursor or a metabolite of testosterone having the same kind of activity as testosterone;
   wherein the testosterone or analog thereof is released within a time interval of 120 seconds upon administration;
   wherein said PDE5-inhibitor is released after said testosterone or analog is released such that the effects of the PDE5-inhibitor and testosterone or analog coincide; and
   wherein said PDE5-inhibitor is released from 1.5 to 4.5 hours after the testosterone or analog is released.

2. The method of claim 1 wherein said testosterone or an analog thereof provides a peak level in the patient's blood circulation of free testosterone or an analog thereof of at least 0.010 nmol/1.

3. The method according to claim 1, wherein the testosterone or an analog thereof is provided in the form of a sublingual formulation.

4. The method according to claim 3, wherein said sublingual formulation further comprises cyclodextrin.

5. The method of claim 1 wherein said female is administered a pharmaceutical formulation comprising:
   testosterone or an analog thereof and a PDE5 inhibitor,
   wherein said analog of testosterone is a precursor or a metabolite of testosterone having the same kind of activity as testosterone;
   wherein said formulation is designed to release the testosterone or analog thereof within a time interval of 120 seconds upon administration;
   wherein said PDE5-inhibitor is released after said testosterone or analog is released such that the effects of the PDE5-inhibitor and testosterone or analog coincide; and
   wherein said PDE5-inhibitor is released from 1.5 to 4.5 hours after the testosterone or analog is released.

6. The method of claim 5 wherein said testosterone or an analog thereof provides a peak level in the patient's blood circulation of free testosterone or an analog thereof of at least 0.010 nmol/1.

7. The method of claim 5, wherein the pharmaceutical formulation is designed for sublingual administration.

8. The method of claim 5, wherein the pharmaceutical formulation further comprises a cyclodextrin.

9. The method of claim 8, wherein said cyclodextrin comprises hydroxypropyl-beta cyclodextrin.

* * * * *